United States Patent [19]

Brugnara et al.

[11] Patent Number: 5,369,014

[45] Date of Patent: Nov. 29, 1994

[54] IN-VITRO METHOD FOR DETERMINING A SURREPTITIOUS USE OF EXOGENOUS ERYTHROPOIESIS STIMULATING AGENTS BY A NORMAL LIVING SUBJECT

[75] Inventors: Carlo Brugnara, Newton Highlands; Margot S. Kruskall, Dover; Mark A. Goldberg, Boston, all of Mass.; Linda A. Chambers, Worthington, Ohio

[73] Assignee: Beth Israel Hospital Assoc., Boston, Mass.

[21] Appl. No.: 930,361

[22] Filed: Aug. 17, 1992

[51] Int. Cl.$^5$ ............................ C12Q 1/02; C12Q 1/00
[52] U.S. Cl. .................................. 435/29; 435/7.25; 435/7.6; 436/817; 436/901
[58] Field of Search .................. 435/7.21, 7.25, 7.6, 435/29; 436/43, 66, 815, 817, 901, 910; 514/6

[56] References Cited

U.S. PATENT DOCUMENTS 4,558,005 12/1985 Goldwasser .................... 435/7

*Primary Examiner*—Michael G. Wityshyn
*Assistant Examiner*—Ralph Gitomer
*Attorney, Agent, or Firm*—David Prashker

[57] ABSTRACT

The present invention is an in-vitro blood assay method for determining the past and/or present use of exogenous erythropoietin by a living subject. The blood assay method detects, identifies, and determines the consequences of using an exogenous erythropoietin to generate an increase in red blood cell production in the living subject and provides a methodology by which to detect and determine both surreptitious as well as authorized therapeutic uses and applications of erythropoietin.

5 Claims, 8 Drawing Sheets

IN-VITRO METHOD FOR DETERMINING A SURREPTITIOUS USE OF EXOGENOUS ERYTHROPOIESIS STIMULATING AGENTS BY A NORMAL LIVING SUBJECT

RESEARCH SUPPORT

The research for the present invention was supported by grants from the Beth Israel Hospital Association, Inc., the Brigham and Womens Hospital Association, and the Trustees of Harvard College.

FIELD OF THE INVENTION

The present invention is concerned with the detection of exogenous erythropoietin use by an in-vitro blood testing methodology; and is particularly directed to the detection of surreptitious erythropoietin administration in a living normal human or animal subject.

BACKGROUND OF THE INVENTION

Erythropoietin or "EPO" is a glycoprotein hormone produced in the kidney and the liver in response to hypoxia; it is a required growth factor for red blood cell production. The existence of a hormone that regulated erythropoiesis was first proposed at the beginning of this century by Carnot and deFlandre. However, because of difficulties in reproducing their results, the idea that a hormone was involved in the regulation of erythropoiesis fell into disfavor until 1943 when Krundieck was able to reproducibly demonstrate the presence of an erythropoietic substance in the serum of anemic rabbits. Subsequently, in 1950, Reissmann [Blood 5:372-380 (1950)] provided strong evidence for the humoral regulation of erythropoiesis using an elegant parabiotic rat model; and in1953 Erslev [Blood 8:349-357 (1953)] provided still more evidence that a hormone, erythropoietin, was involved in the regulation of red cell production. Erslev demonstrated that plasma taken from an anemic rabbit and injected into a non-anemic rabbit caused a dose-dependent reticulocytosis and increase in erythroid precursors in the bone marrow. Prior to birth, EPO is produced primarily in the liver; whereas after birth, the kidney becomes the major endogenous EPO producing organ.

Despite considerable effort, attempts at purification of EPO were elusive until 1977 when Goldwasser and his colleagues [Miyake et al., J. Biol. Chem. 252:5558 (1977)] were able to isolate approximately 10 mg of homogeneous human EPO and subsequently determined a partial amino acid sequence. This achievement subsequently led to the isolation of genomic and cDNA clones of human and mouse EPO.

The human EPO was cloned in 1985 by two independent groups [Jacobs et al., Nature 313:806-810 (1985); Lin et al., Proc. Natl. Acad. Sci. USA 82:7580-7584 (1985)]. The sequence is highly conserved between mouse and man providing an indication of its evolutionary importance. The human EPO gene encodes a protein of 193 amino acids. Following cleavage of a 27 amino acid N-terminal "leader" sequence, the mature protein has a calculated molecular weight of about 18,400. However, human EPO contains approximately 40% carbohydrate, giving it a molecular weight of approximately 30,400 daltons. Post-translational glycosylation is clearly required for in vivo function. In addition, human EPO contains two disulfide bonds, at least one of which appears to be essential for the function of the molecule. Recombinant human EPO or "r-HuEPO" has been mass produced in Chinese hamster ovary cell lines and is indistinguishable from the native molecule. In clinical trials, to date, no patients have developed antibodies to r-HuEPO, thereby showing that for all intents and purposes r-HuEPO is virtually identical to the native endogenous human EPO.

Hypoxia is the chief stimulus for in vivo production of EPO. In response to the sensing of hypoxia in the kidney and the liver, increased EPO gene transcription in vivo leads to increase EPO mRNA and an increased production and secretion of EPO protein. The hormone (EPO) travels to hematopoietic tissues where it binds to its receptor on erythroid progenitor cells and stimulates them to proliferate and differentiate into mature red blood cells. This results in an increase in the oxygen carrying capacity of the blood, alleviating the hypoxic stimulus, and providing a complete feedback loop for regulation of EPO gene expression and red blood cell production. In anemic patients, serum EPO levels have been shown to be inversely proportional to the hematocrit or hemoglobin concentration providing that renal function is normal. The level of EPO in the plasma correlates with the rate of production of new erythrocytes by the bone marrow. Failure to increase the amount of circulating EPO in response to hypoxic stress can lead to anemia.

Prior to the cloning of the EPO gene, measurement of endogenous EPO in plasma and serum relied primarily on in vivo and in vitro bioassays. The flaw of relying solely on bioassays has been clearly demonstrated by Sytkowski et al. who discovered a renal cell carcinoma cell line with erythropoietin-like activity but which was immunologically distinct from erythropoietin when assayed by a sensitive and specific radioimmunoassay. Although an accurate immunologic assay for erythropoietin was first developed in 1979, readily available assays have only recently come into being. Hence, up until the past few years, there continued to be many studies which relied solely on bioassays to assess erythropoietin serum concentrations in various clinical settings. However, more and more studies are now performed using immunoassays as the technique of choice. Most of these studies have employed immunoassays with polyclonal antisera and, most recently, recombinant standards. Using such assays, normal serum levels of EPO lie in the vicinity of 4-30 mU/ml; with different assays yielding slightly different, but overlapping, normal ranges. Moreover, serum EPO levels have been confirmed to be inversely proportional to the hematocrit or hemoglobin concentration, providing that the patient has normal renal function.

Of particular interest is the finding that when normal individuals are sequentially phlebotomized (up to one unit of blood, twice per week for three weeks), they generally increase their circulating EPO levels only to a modest degree. This observation reveals an important aspect of the natural regulation of erythropoiesis. In response to progressive anemia, and hence increasing degrees of tissue hypoxia, the increase in endogenous EPO production is gradual and graded. The low levels of EPO which are always present appear to be sufficient to allow for a basal rate of erythropoiesis. Thus, relatively small losses of blood, such as a one unit blood bank donation, stimulate in vivo EPO production only to a small degree; and the red cell mass slowly returns to its steady state level with only a small change in the rate of erythropoiesis. It is only after a major blood loss that a markedly increased production of EPO and rate of erythropoiesis ensue.

Within the last few years, however, a new phenomenon has presented itself. Since in-vivo use of exogenous erythropoietin, and typically recombinant, human EPO became recognized as stimulating erythropoiesis; a surreptitious use of recombinant EPO has become a favored elicit drug by athletes, both amateur and professional. The use of such elicit drugs is not permitted by almost all athletic bodies, and in particular by the International Olympic Committee and its affiliates. Nevertheless, the surreptitious use of EPO is believed to be common because, although the effects of the drug are longlasting enduring for many weeks, EPO has a relatively short half-life in-vivo within the body, lasting only a few hours to a few days at most. In addition, because many coaches as well as athletes are medically informed today, the prevalent practice now is to discontinue the surreptitious use of EPO a calendar week or so before the upcoming sports event. Thus, direct chemical determinations for EPO in the blood appear normal on the day of the sport event, it being impossible to distinguish between endogenous EPO made in-vivo and recombinant EPO whose use was discontinued earlier in time.

Insofar as is presently known, however, there are no reported investigations or published procedures which even suggest that an effective method and protocol for detecting a surreptitious use of erythropoietin might be possible. Given the ever increasing authorized and clandestine use and administration of rEPO, the generation of a rapid and reliable methodology by which to determine whether a living subject has been using EPO would be generally recognized and accepted as a major advance and long desired development by persons working in this field.

SUMMARY OF THE INVENTION

The present invention provides an in-vitro method for identifying the surreptitious use of an exogenous agent to generate an increase in red blood cell production in a living normal human or animal subject, said method comprising the steps of:

obtaining an aliquot of the blood circulating within the living subject;

testing said aliquot of blood to establish an absence of anemia in the living subject, said testing comprising at least one parameter selected from the group consisting of hematocrit value and blood hemoglobin concentration, a test result that lies within the normal range of values for that parameter establishing the absence of anemia in the subject;

evaluating said aliquot of blood to determine the presence of at least normal total body iron stores in the living subject, said determination comprising at least one indicator selected from the group consisting of serum iron value, serum transferrin value, serum transferrin saturation, serum ferritin value, and red blood cell ferritin concentration, an evaluation result that lies within the normal range of values for that indicator establishing the presence of at least normal total body iron stores in the subject; and analyzing said aliquot of blood to establish the presence of at least one abnormality within the individual red blood cells of the living subject, said abnormality being at least one selected from the group consisting of a less than normal concentration of hemoglobin within individual red blood cells and a greater than normal content of zinc protoporphyrin within individual red blood cells, whereby the established absence of anemia, and the established presence of at least normal total body iron stores, and the established presence of at least one abnormality within individual red blood cells collectively identify that normal living subject as a surreptitious user.

BRIEF DESCRIPTION OF THE FIGURES

The present invention may be more easily and completely understood when taken in conjunction with the accompanying drawing, in which.

DETAILED DESCRIPTION OF THE PRESENT INVENTION

Figure 1A:
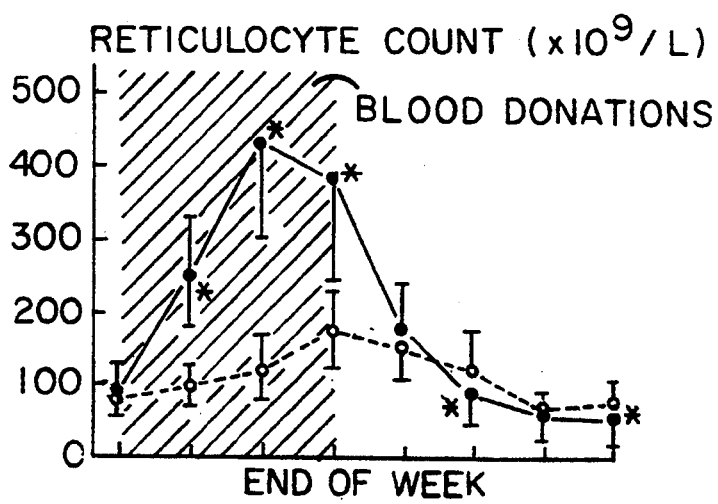
FIGS. 1A-1C are graphs illustrating the absolute reticulocyte count at baseline and at the end of each week of the study for test subjects taking rEPO.

The present invention is a diagnostic/clinical test method performed in-vitro which detects, identifies, and determines the use by a living human or any other mammal of exogenous erythropoietin or any other exogenous agent or substance which is able to cause a similar increase in the production of red cell progenitors and mature red cells by the bone marrow or any other erythropoietic tissue. The consequence of using exogenous erythropoietin or similarly acting agents is the increase in the red blood cell production within the human or animal. The purpose and the achievement of the present invention is the determination that one specific normal subject has employed one or more administrations of exogenous erythropoietin or other agent to generate and achieve an increase in the number of the circulating red cells at a time when the exogenous use of EPO can not be detected by assays measuring the plasma level of this hormone in such subject or animal; and the plasma concentration of EPO are within those ranges which are normally achieved via the endogenous production of erythropoietin in comparable humans or animals.

It will be recognized and appreciated that the present invention, an in-vitro assay method, provides a number of major advantages and unusual benefits to the user, which were unknown and unavailable to the medical practitioner, the clinician, the veterinarian, or the laboratory technician previously. These unique advantages and benefits include the following:

1. The present invention employs an aliquot of circulating blood taken from one specific living subject as the material which is to be tested and evaluated empirically. The methodology is thus a blood test procedure and technique. It focuses upon the red blood cells and their characteristics and composition as the bases for the testing; and on the blood plasma indicators and parameters which reflect the extent of iron stores normally available in a living subject. No other body fluids such as urine, sputum, or otherwise are required or desired. Only a single aliquot of circulating blood, taken conventionally; which is typically divided into one or multiple tubes containing the appropriate anticoagulants or preservatives and kept from deterioration using conventional practices, is the single and exclusive material needed to perform the test procedure.

2. The present blood testing methodology will detect, identify, and determine the presence of red cells produced by the bone marrow under stimulation by exogenous erythropoeitin or any other exogenous hormone substance or agent capable of stimulating red cell production (with a mechanism of action similar or different from that of EPO) when conventional plasma or serum determinations of circulating levels of erythropoietin or other specified agents fail to demonstrate their presence in the sample. This method will also detect the use of exogenous erythropoeitin even in autologous blood transfusion, when used to increase the red blood cell count and thus physical endurance even if the blood is not transferred for many months after collection.

3. The present method is able to detect use of exogenous erythropoietin and any other substance or hormone which increases the production of red cells by the bone marrow. Exogenous EPO, by definition, is any active erythropoietin molecule, fragment, fused fraction, analog, or derivative which was not generated in-vivo by that specific individual. A subject's own in-vivo produced EPO is thus "endogenous" EPO, which is measurable in picogram or 'pg' quantities at any time in the living subject. Therefore, the term "exogenous" EPO includes both EPO made in-vivo by another person which is later transferred by blood transfusion; and all active entities obtained by chemical isolation and purification which are then administered as a purified or partially purified preparation subsequently. In addition, EPO manufactured by recombinant DNA techniques, the most prevalent form of manufacture and production today, also clearly falls within the definition of "exogenous" erythropoietin. Recombinant, second generation EPO, which share similarities with the original molecule, but have increased potency, also clearly fall within the definition of exogenous EPO. Moreover, any other substance, hormone, or agent which affects the bone marrow and directly or indirectly induces an increased production of red cell precursors (and ultimately red cells) which have cellular characteristics similar to these caused by exogenous EPO administration also clearly fall within the definition of exogenous stimulators of red cell production. The use of any or all of these exogenous EPOs and other stimulatory compounds by a living subject may be routinely and accurately detected and determined using the present method. Furthermore, the use of this technique is not limited to humans but can be applied to any other mammal, provided that the red cells produced by the bone marrow or any other erythropoietic organ after stimulation by EPO or any other active substance share the abnormal characteristics which are present in human subjects.

4. The present blood testing methodology will detect, identify, and determine one or more uses and administrations of exogenous erythropoietin or other active agents by a specific living subject. The use may have been only a single administration or include administrations on multiple occasions. The use may be on a fixed time schedule, frequent but unscheduled, irregular, or random. In addition, the use of exogenous erythropoietin or other active agents may be present and ongoing; have occurred recently within days or weeks but is not presently ongoing; or have occurred in the past without any recent or present administrations up to a period corresponding to and not longer than the life span of normal circulating erythrocytes (120 days). Conversely, as is expected in some testing circumstances, if an administration of exogenous erythropoietin occurred within the prior 24–48 hours sufficient to have stimulated the bone marrow and induced new red blood production, the test methodology described herein will detect the use of the exogenous erythropoietin or other active agent by that individual. The effective value of the present testing methodology thus provides accurate information and data for any use of exogenous erythropoietin or other substance by one particular person or living subject if such use occurred one day or less than 120 days prior to taking the blood sample for testing purposes, provided that an appreciable production of new red blood cells was initiated.

5. The present testing methodology employs a variety of different morphological and chemical test procedures as a battery of assays, all of which are individually conventionally known and accepted generally. Each of the individual procedures and test protocols have been verified by many persons over a period of years; and provide parameters and indicators which are frequently employed today for many different diagnostic and clinical measurements and evaluations in the laboratory. In addition, much automated instrumentation has come into existence and is commonly employed in performing these morphological and chemical assays themselves. The development of flow cytometric techniques, optical instruments, and practices has enhanced and increased both the speed and accuracy of these conventionally known procedures such that they may be employed concurrently with a minimum of labor and technical skill. By employing these conventionally known procedures in specific combinations for evaluation purposes, the present blood assay methodology employs these conventional techniques to provide indices and parameters by which the determination of exogenous erythropoietin are made in an accurate and reliable manner.

6. The present invention does not detect exogenous erythropoietin directly as a chemical substance. Instead, the present invention relies upon identifying the consequences of using exogenous EPO in-vivo, which are the presence of red cells with characteristics of iron deficient cells in the absence of other signs supporting the presence of iron deficient anemia. On this basis and distinction, surreptitious administrations of exogenous EPO and other stimulating agents may be detected and identified. It will be recognized, that while monitoring of patients which have been administered recombinant EPO as a therapeutic agent can be achieved by measuring EPO plasma levels and comparing them with baseline levels in the absence of EPO, there is no present procedure or technique which will detect a surreptitious use of EPO or of any other active substance or compound which has induced an increase in the production of red cells by the bone marrow. This technique will therefore indirectly detect any other natural or artificial substance, compound, or hormone which is able to increase production of the red cells by the bone marrow, if these cells have the abnormal characteristics observed in human subjects taking EPO.

By its very nature and essence, the present invention is a methodology comprised of manipulations employing test procedures, apparatus, morphological examination of blood constituents, and a variety of different chemical reactions which must be performed accurately and successfully. It is therefore imperative that the user be familiar and comfortable with laboratory diagnostic tests, assay instrumentations, and evaluation procedures currently employed in hematology; and with the medical and clinical settings and circumstances involving living human beings relevant to erythropoiesis and the production of red blood cells. The range and variety of medical information and background which are critical and essential to a proper and complete understanding of the present invention are fully described in the published medical and scientific literature. A range of authoritative texts have been relied upon for the information which follows hereinafter. These are represented by the following: Fundamentals of Clinical Chemistry, third edition, Norbert W. Tietz (editor), W. B. Saunders Company, 1987; Hematology, fourth edition, William S. Beck (editor), N.I.T. Press, Cambridge, Mass., 1987; A Manual of Laboratory Diagnostic Tests, second edition, Frances C. Fischback (editor), J. B. Lippincott Company, Philadelphia, 1984; and Hematology, 4th edition, McGraw-Hill Inc., 1990. The text of each of these publications individually, in its entirety, is expressly incorporated by reference herein.

I. Terminology and Definitions

To avoid ambiguity of language, imprecise terminology, and vague definitional contexts, a listing of technical terms, definitions, and conventional background information is provided below. The description of the present invention will employ and rely upon these terms, definitions, and contexts.

Erythropoiesis: The generation of red blood cells in the bone marrow.

Reticulocyte: an immature red cell recently released into the peripheral blood from the bone marrow.

Anemia: a decreased number of erythrocytes or a decreased hemoglobin content of blood;

Polycythemia: a greater than normal number of erythrocytes in the blood;

Hemoglobin (HB): a spheroidal protein that consists of four subunits, two pairs of identical polypeptide chains, each with a cleft or pocket on its exterior. The cleft contains a heme or iron-protoporphyrin group that is the site of oxygen uptake and release.

Hematocrit (HCT) or packed cell volume (PCV): this parameter identifies and expresses the space occupied by packed red blood cells and is expressed as the percentage of red blood cells in a volume of whole blood. This value and number can be obtained either by measuring the ratio of red cells to total blood following centrifugation of an aliquot of blood; or by measuring the mean corpuscular volume of a population of red cells and then multiplying that result by the number of red blood cells in an aliquot of blood.

Red blood cell indices: the red blood cell indices are used to define the size and hemoglobin content of the red blood cell. They consist of the mean corpuscular volume (MCV), the mean corpuscular hemoglobin (MCH), and the mean corpuscular hemoglobin concentration (MCHC). Typically, these tests are determined using the same blood sample as employed for hemoglobin, hematocrit, and red blood cell counting purposes.

Mean corpuscular volume (MCV): The MCV expresses the average volume occupied by a single red cell in cubic microns. The MCV indicates whether the red blood cells appear normal, microcytic (smaller than normal), or macrocytic (larger than normal). If the MCV is less than 87 $\mu m^3$, the red cells are microcytic; if greater than 103 $\mu m^3$, the red cells are macrocytic; and if within the normal range, the red blood cells are normocytic.

Mean corpuscular hemoglobin concentration (MCHC): The MCHC is a measure of the average concentration of hemoglobin in grams per deciliter of red blood cells.

Mean corpuscular hemoglobin (MCH): The MCH is a measure of the average weight of hemoglobin in the red blood cell. This index is of value in diagnosing severely anemic patients, but is not as useful as the MCHC value because the red cell count is employed in its calculation and the red cell count is deemed not to be always accurate. The MCH value is expressed as picograms of hemoglobin per red blood cell.

The red blood cell indices collectively are used as an aid in differentiating anemias. When these are used together with an examination of the red cells on the stained smear, a clear picture of red cell morphology may be ascertained.

Iron: Iron is essential in life and in man is required for the production and function of hemoglobin. The average adult body contains a total of about 4 grams of iron, the range being between 2–5 grams. For general purposes, a 70 kg man is said to contain 50 mg/kg or 3.5 grams of total body iron.

Iron is absorbed in-vivo by mucosal cells in the gastrointestinal tract and transported into the plasma. Here, metabolized iron is moved from one organ to another as Fe(III) bound to a plasma protein called "apotransferrin." The apotransferrin-Fe(III) complex is called "transferrin." Iron in storage form in various cells is about 800 mg in men and 0–200 mg in women. Ferritin is the major iron-storage compound; it occurs in nearly all body cells. The apoferritin shell surrounds an interior ferrin oxyhydroxide crystalline core that contains 2,000–4,000 Fe(III); nonenzymatic reduction of Fe(III) to Fe(II) occurs as iron is released from ferritin. The minute concentration of ferritin in serum is an indicator of total body storage iron.

Iron deficiency: a clinical state in which the total body iron is diminished. A determination of iron deficiency is made by measurements of serum iron concentration and total iron-binding capacity. Alternatively, assay of serum ferritin concentration has shown to be a sensitive and reliable means of demonstrating the disorder. Free erythrocyte protoporphyrin or zinc protoporphyrin concentration is increased in persons with iron deficiency. The parameters used to determine iron status are the following:

1. Serum iron concentration: a parameter and value which connotes the Fe(III) bound to serum transferrin. Serum iron concentration is decreased in patients with iron deficiency anemia. Greater than normal concentrations of serum iron occur in iron overload disorders such as hemochromatosis.

2. Total iron-binding capacity: this parameter and value is a measurement of the maximum concentration of iron that serum proteins, particularly transferrin, can bind. The serum total iron-binding capacity varies in disorders of iron metabolism and typically increases in iron deficiency. Normally only about one-third of the iron-binding sites of transferrin are occupied by Fe(III).

3. Serum ferritin: serum ferritin is well correlated with body iron stores. A serum ferritin value less than 10 μg/dL is diagnostic of iron deficiency; and values between 10-20 μg/dL suggests iron deficiency. 4. Zinc protoporphyrin: zinc protoporphyrin (or free erythrocyte protoporphyrin) is an indirect measure of iron incorporation into hemoglobin. As iron deficiency develops, a large number of hemoglobin molecules incorporate zinc rather than iron into their structure. Thus, a zinc protoporphyrin value greater than 75 mg/dL of red cells suggests an iron deficiency.

A listing and summary of the normal range of values for each of the above listed parameters is provided by Tables 1 and 2 herein.

TABLE 1

NORMAL BLOOD VALUES

| Blood Entity | Normal Range |
|---|---|
| Red blood cell count (RBC) | Men: 4.2–5.4 mln/cu mm |
| | Women: 3.6–5.0 mln/cu mm |
| Hematocrit (HCT) | Men: 40–50% |
| | Women: 37–47% |
| Hemoglobin (Hgb) | Men: 12–15 g/100 ml |
| | Women: 14–16.5 g/100 ml |
| Red blood cell indices: | |
| a. mean corpuscular volume (MCV) | 87–103 cu um/red cell or 3 um/red cell |
| b. mean corpuscular globin concentration (MCHC) | 32–36% |
| c. mean corpuscular hemoglobin (MCH) | 27–32 pg |
| Reticulocyte count | Adult Male: 0.5–1.5% of total erythrocytes |
| | Adult Female: 0.5–2.5% of total erythrocytes |
| Zinc protoporphyrin or free erythrocyte protoporphyrin | 30 mg/dl red cells |
| Total (tranferrin) iron-binding capacity (TIBC) | 250–450 mg/dl |
| Serum iron (SI) [transferrin-bound iron] | 0.004 g total or 42–135 mg/dl (0.1% of total body iron) |
| Transferrin saturation (TS) | 0.25–0.60 |
| Red blood cell ferritin | 13–137 ag*/cell |
| Serum (plasma) ferritin concentration (SF) | 10–280 ug/l |

*ag = attogram ($10^{-18}$ grams)

TABLE 2

STAGES OF IRON DEFICIENCY DEVELOPMENT

| Stage | Reduced Fe Stores | Anemia | Hypochromic Microerythrocytes |
|---|---|---|---|
| Normal | No | No | No |
| Iron depletion | Yes | No | No |
| Iron deficiency anemia (early stage) | Yes | Yes | No |
| Iron deficiency (advanced stage) | Yes | Yes | Yes |

Given the definitions, terminology, and background information summarized herein, the details of the present invention may now be more easily understood and appreciated. To aid in a complete and thorough comprehension, the detailed description will be presented in the following order: an identification and characterization of known exogenous erythropoiesis simulating agents; a description of the uses and applications for the present invention; a disclosure of the applications and use circumstances under which the present invention is advantageously employed; a description of the essential criteria and markers which identify exogenous erythropoietin use; protocols summarizing the various assay procedures and techniques employed when performing the present invention; a scoring and evaluation criteria for making a determination; and experiments and empirical data demonstrating the utility and value of the present invention. Each will be described in detail individually.

II. Exogenous Erythropoiesis Stimulating Agents

The present methodology is able to detect the in-vivo consequences of a living subject's using one or more exogenous agents which are pharmacologically active and capable of stimulating new red blood cell production. The phyllum of stimulating agents able to initiate and generate new red cells is diverse and varied in chemical structure and composition; can utilize a range of different mechanisms of action in-vivo; and is obtained from unrelated sources as exogenous agents in a purified or partially purified state.

At least two unrelated chemical families are presently known: erythropoietin and erythropoietin-like substances; and water-soluble salts of transition metals. Each family will be described individually.

A. Erythropoietin and Erythropoietin-Like Substances

This family chemical formulation and overall structure is based upon endogenous erythropoietin, synthesized in-vivo by humans and animals. Exogenous erythropoietin (EPO) is thus any molecule identical or similar in whole or in part to that molecule produced in-vivo. Thus, exogenous EPO includes EPO made in-vivo by another person which is later transferred by blood transfusion or other intravenous transfer means; EPO in whole or in part obtained or isolated by chemical isolation and purification techniques which are then administered as a purified or partially purified preparation; and EPO of any type manufactured using recombinant DNA techniques which is administered alone or as part of a pharmaceutical formulation.

In addition, erythropoietin-like substances constitute a major portion of this chemical family. Recognizing that EPO is a polypeptide comprised of amino acid residues in positioned sequence order and orientation, a diverse range of different pharmacologically active amino acid fragments, fused fractions, analogs and derivatives of EPO can be prepared using conventionally known techniques and instrumentation. Thus, an EPO fragment is any amino acid sequence shorter in length than the entire EPO molecule and which is biologically active to stimulate erythropoiesis. In comparison, a fused fraction is a fusion of two or more amino acid sequences nominally present in the intact EPO molecule which have been isolated and covalently bonded together as a single entity by laboratory protein synthesis methods or by recombinant fused-gene cell culture techniques. Conversely, an EPO analog is a polypeptide whose amino acid sequence is similar in meaningful degree but not identical to a naturally occurring EPO amino acid sequence. Finally, an EPO derivative is the erythropoietin molecule or any portion of the complete EPO structure which has been modified by the addition (or deletion) of one or more substituents, radical groups, atoms, or other chemical moieties—such as a hydrogen, oxygen, sulfur, or halogen atom; a nitrogen containing group; a carbonyl group; or a carbohydrate or lipid residue. Cumulatively and collectively these constitute erythropoietin-like substances, all of which share a degree of chemical overlap with endogenous EPO from human or animal sources; and all of which retain a measurable degree of potency to stimulate new red cell production after being administered to a living subject. All of these chemical entities are deemed to be detectable and thus lie within the scope of the present invention.

B. Water-Soluble Salts of Transition Metals

The second chemical family of stimulating agents detectable using the present methodology comprises water soluble salts of transition metals. These transition metals preferably are manganese (Mn), cobalt (Co), and nickel (Ni); and also include titanium (Ti), vanadium (V), and chromium (Cr). Most, if not all, water-soluble salts of these transition metals are believed to be stimulators of red cell production when administered in suitable concentration in-vivo. The salts thus include halides and most preferably chloride salts; carbonate and bicarbonate salts; sulfides, sulfites, and sulfates; nitrogen atom containing salts; oxides; and other conventional salt formats and formulations generally biocompatible and useful in-vivo.

III. Applications and Uses for the Blood Assay Methodology

The present blood assay method for determining the use of exogenous erythropoietin or other erythropoiesis-stimulating agents to generate an increase in red blood cell production by the blood marrow in a living subject can be most usefully employed in detecting surreptitious uses of exogenous stimulating agents.

The most common surreptitious use and application by living subjects is probably the human use of recombinant EPO by amateur and professional athletes. The administration of rEPO increases production of red blood cells in-vivo, which is considered by many to be beneficial in endurance sports and contests. The use of such drugs is not allowed by the International Olympic Committee and many other amateur athletic bodies and organizations. Nevertheless, it is presently believed that surreptitious use of rEPO is common because: first, although the effects of erythropoietin administration are longlasting over many weeks, EPO has a short half-life in-vivo within the living body and lasts only a few hours to a few days; and second, presently employed blood tests which directly measure plasma levels of circulating EPO would be negative regarding EPO use if the person discontinued using or administering the EPO a week or even several days before the date of testing for the sports event itself. A representative listing of some, but not all, surreptitious uses and applications of exogenous erythropoietin is provided by Table 3.

TABLE 3
SURREPTITIOUS USE OCCASIONS

1. Regimented, frequent, or irregular use by amateur athletes for any recognized sport, contest, or event.
2. Regimented, frequent, or irregular use by professional athletes for any recognized sport, contest, or event.

TABLE 3-continued
SURREPTITIOUS USE OCCASIONS

3. Casual use by body builders, health enthusiasts, or survivalists.
4. Casual use by "weekend" athletes or irregular exercise programs.
5. Casual or sporadic use by persons not performing any exercise routinely for specific occasions of personal value or importance.

IV. Essential Criteria and Markers of the Blood Assay Method

The present invention employs a series of specific morphological and chemical blood assays whose data and results collectively identify the in-vivo consequences of erythropoietin or other erythropoiesis stimulating agent usage by medically normal subjects—a usage which results in iron-deficient and underhemoglobinized red blood cells within the otherwise normal body. As empirically demonstrated by the experiments and data provided hereinafter, healthy persons having normal iron stores, whether taking or avoiding iron supplements in their diets, produce abnormal iron-deficient and underhemoglobinized erythrocytes when administered exogenous EPO. These abnormal red cells are produced in-vivo as a direct consequence of exogenous EPO or other agent administration because the rapid rate of red blood cell production initiated by the exogenous agent is too great for cellular incorporation of a normal amount of iron and a normal amount of hemoglobin. Thus, only grossly, intentionally iron-overloaded living subjects are still able to make normal red blood cells after being given an exogenous erythropoiesis stimulating agent such as rEPO.

The battery of tests include the following:

1. A determination of the hematocrit and/or concentration of hemoglobin in the circulating blood using standardized manual or automatic instrumentation techniques. These determinations will demonstrate the absence of anemia in the living subject. The absence of anemia for humans is identified and shown by a hematocrit (HCT) value greater than 38% (female) or 41% (male); and/or a hemoglobin concentration value greater than 12.5 (female) or 13.5 (male).

2. A determination of total body iron stores. The indicators to be measured include at least one, and preferably several, assays of a blood sample or aliquot selected from the group consisting of serum iron, transferrin, transferrin saturation, serum ferritin, and any of the other determinations known to assess the extent of body iron stores in the living subject. The empirical determinations will show the absence of any abnormalities typically associated with an early stage iron deficiency anemia or a more advanced stage iron deficiency—as represented by low serum iron values, low serum ferritin values, reduced ferritin levels, reduced red cell ferritin content, increased transferrin values, and/or decreased transferrin saturation values. This determination will thus establish the presence of at least normal total body iron stores in the subject under test.

3. A determination of the red cell volume and red cell hemoglobin concentration measured on a cell by cell basis—preferably using flow cytometry instrumentation and a graphic plot of the hemoglobin concentration as a function of red cell volume on a cell by cell basis. This determination allows a comparison of the relationship between these two parameters (red cell volume and individual red cell hemoglobin concentration) for the blood sample under examination. A most desirable format and criteria is a histogram of the hemoglobin content of the red cells, derived from the cell by cell measurements of hemoglobin concentration and cell volume. This empirical determination will show the presence of red cells with an abnormally low hemoglobin concentration for a given cell volume; and/or an abnormally low hemoglobin content per individual cell—either one or both of which are typical characteristics of iron deficient erythropoiesis.

4. As an alternative to cell by cell measurements of red cell volume and hemoglobin content to establish cellular abnormality, one can analyze the zinc protoporphyrin (ZPP) content of the red cells in the blood sample under examination as another indicator of cellular abnormality. The determination may include ZPP analysis of the whole blood sample; or of the 15% lightest fraction and the 50% densest fraction of the same sample; or of any other combination of density fractions which will distinguish between young and old red blood cells. This determination will reveal markedly elevated zinc proporphyrin values, particularly in the lightest cell fractions in contrast to minimally elevated or normal ZPP values in whole blood and normal values for the densest fraction of red blood cells.

Each of the above identified blood or cellular determinations is to be evaluated and judged with respect to the normal range of values previously given within Table 1 herein. An abnormal decrease is recognized as being a numerical value or determination which is lower or less than the lowest limit within the normal range; similarly, an empirical determination is also abnormal if it is higher than the upper numerical limit provided by the normal range of values.

It should be noted that the conclusion of surreptitious usage is rendered by the present methodology by performing the battery of assays collectively and currently. In particular, it should be noted that an empirical showing of abnormal red cell features (elevated ZPP values and/or diminished hemoglobin concentration per red cell volume on a cell by cell basis) is not sufficient in and of itself to satisfy the requirements of the present method. To the contrary, the method requires, via an empirical evaluation of a blood sample from the living subject, that an absence of anemia and the presence of at least normal total body iron stores be established and exist concurrent with at least one demonstrated cellular abnormality within individual red blood cells in the same blood aliquot. In this manner, and by this empirical demonstration of hematological normalcy in gross concurrent with a demonstrated abnormalcy within individual red cells (underhemoglobinized cells with increased ZPP values), does the present battery of assays provide accurate and reliable evaluations and judgements.

Recognizing that conventional test techniques and protocols are to be employed for empirically testing and obtaining results for each blood constituents, blood constant, and blood cell type a sample score sheet or empirical data recording sheet is illustrated by Table 4.

TABLE 4
CRITERIA FOR SCORING AND EVALUATION IN HUMANS

| 1. Absence of Anemia | Value[f] |
|---|---|
| normal hematocrit | $\geq 41\%$ (male) |
| | $\geq 38\%$ (female) |
| normal hemoglobin | $\geq 13.5$ gr. % (male) |
| | $\geq 12.5$ gr. % (female) |
| 2. Normal Total Body Iron Stores | |
| normal serum iron | $\geq 40$ ug/dL |
| normal or elevated serum transferrin saturation | $\geq 15\%$ |
| normal or elevated serum ferritin | $\geq 20$ |
| normal serum transferrin | 200–350 mg/dl |
| normal red blood cell ferritin | $\geq 11.5$ ag*/cell (male) |
| | $\geq 8.8$ ag*/cell (female) |
| 3. Abnormal Red Blood Cell Features | |
| Underhemoglobinized individual red blood cells, reticulocytes, or other red cell population Increased zinc protoporphyrin content within red blood cells | |

[f]Reference: Cazzola, M., "Biological and Clinical Significance of Red Cell Ferritin," Blood 62:1078–1087 (1983).
*ag = attogram ($10^{-18}$ grams)

V. Preferred Protocols

1. Determination of the Hemoglobin and Hematocrit
A. Hemoglobin (manual method):
  1. Reagents and equipment:
     a. Cyanmethemoglobin reagent (commercially available by this name of as "Drabkin's" reagent)
     b. Test tubes
     c. Disposable pipettes (0.02 mL)
     d. Colorimeter or spectrophotometer
     e. Sample—whole blood, anticoagulated
  2. Procedure: Add 5.0 mL of cyanmethemoglobin reagent into a test tube; add 0.02 mL of whole blood. Mix well and allow to stand for ten minutes. Transfer to a cuvette and read at a wavelength of 540 nm. Use cyanmethemoglobin alone (without blood) to set the blank transmission at 100%. The result is determined in comparison to a calibration chart (made from testing dilutions of a blood sample of known hemoglobin concentration.
B. Hematocrit (microhematocrit manual method):
  1. Reagents and equipment:
     a. Capillary hematocrit tubes, length 7 cm, bore 1 mm
     b. Clay, to seal one end of the tube
     c. Centrifuge (capable of achieving 11,500–15,00 RPM) with an appropriate head for the capillary tubes
     d. Whole blood, anticoagulated.
  2. Procedure: Allow well-mixed blood to enter two capillary tubes until ⅔rds full. Seal one end of each tube with clay. Place tubes in centrifuge head with clay ends pointed out; centrifuge for 5 minutes. Read, using a microhematocrit tube reading device (or measure height of red cell column, and divide by height of blood column).
C. Hematocrit and hemoglobin, by automated technology:
  1. Reagents and equipment: Any of a variety of commercially available automated instruments may be used to determine these two tests (for example, the Hemalog-D, Technicon H6000, Technicon H-1; all made by Technicon Instruments, Tarrytown, N.Y.). These instruments incorporate systems for measuring individual cell size and counts using electrical impedance. In addition, most machines also make hemoglobin determinations using an automated version of the manual method described above. The hematocrit is a calculated measurement based on machine measurements of individual red cell volumes multiplied by the number of red cells per mL. An anticoagulated specimen of whole blood (preferably drawn in EDTA) is used for these tests.

2. Procedure: Use per manufacturer's instructions. Typically 100 microliters of blood is required for each determination.

2. Determination of Serum Iron, Total Iron Binding Capacity, Transferrin Saturation, Serum Ferritin, and Red Cell Ferritin A. Serum iron: Described below is an assay which measures iron by reducing it, in acid conditions, to $Fe^{+2}$; and then reacting it with derrozine, a dye which forms a magenta-colored complex with iron. The complex absorbs light maximally at 560 nm. The results are expressed in micrograms/dL.

1. Reagents and instruments: Cobas-Bio centrifugal analyzer (Roche Analytical Instruments, Inc., Nutley, N.J.); iron standard solutions; iron buffer reagent (Sigma Catalog No. 565-1); iron color reagent (Sigma catalog no. 565-3); Cobas sample cups, racks, tipcs, cuvette rotors; patient serum or plasma.

2. Procedure: The procedure is highly automated; a technologist must only load serum or standards into cups on various positions on the sample trays, and choose the program which carries out the test described above.

B. Total iron binding capacity (also called transferrin): A nephelometric procedure is described, which involves the formation of an antibody-antigen complex, where transferrin is the antigen. The increase in light scatter caused by the developing antibody-antigen reaction is measured as a peak rate signal, which are converted into concentration units by the nephelometer.

1. Reagents and instruments: Beckman Array Protein System nephelometer (Beckman Instruments, Inc., Brea, Calif.); Beckman transferrin (TRF) antibody reagent (Catalog No. 449420); Beckman buffer (Catalog No. 663630) and calibrator (Catalog No. 449730); Array TRF antibody card, calibrator card, and dilution segments (Catalog No. 757413); patient serum or plasma.

2. Procedure: The procedure is highly automated, and manufacturer's instructions should be followed with regard to placement of samples and evaluation of results. Transferrin (in mg/dl) is converted to total iron binding capacity (TIBC, in micrograms/mL) by multiplying by 1.2.

C. Transferrin saturation: This figure is derived by dividing the serum iron by the serum transferrin (without regard to units of measure), and expressing the resulting figure as a percentage (for example, serum iron 50 micrograms/dL, transferrin 250 mg/dL; therefore, transferrin saturation=20%).

D. Serum ferritin: Ferritin can be measured with an immunoradiometric, immunoenzymatic, or immunofluorometric sandwich assay. The last technique is described as a representative assay:

1. Reagents and equipment:
   a. DELFIA ferritin kit (LKB-Wallac No. 1244-008; Wallac Oy, via Pharmacia Diagnostics, Columbia, Md.) including ferritin standards, anti-ferritin-europium labelled; enhancement solution; and wash solutions.
   b. LKB-Wallac 1232 Delfia fluorometer (Pharmacia Diagnostics).
   c. LKB-Wallac Delfia plate washer (Product No. 1295-024)
   d. Microtiter plate shaker
   e. Timer, pipettes, and QC material
   f. Patient serum 2. Procedure: The following is a brief summary of manufacturer's instructions included with the fluorometric assay kit. To microtiter wells coated with IgG-anti-ferritin are added patient serum samples, standards, and controls. Following incubation and washing, europium-conjugated IgG-anti-ferritin is added. Following a further incubation and washing, a fluorescence enhancing solution is added, and the amount of fluorescence is read. The result in each well is reported in microgram/L in relation to a standard curve constructed during the same assay.

E. Red cell ferritin

1. Reagents and instruments: The same materials as are used in D (serum ferritin) are required; however, the blood sample must be a hemolysate prepared from an aliquot of anticoagulated whole blood (ideally in EDTA), rather than serum. For calculating the result, the hemoglobin concentration of the lysate must be measured; and the MCH of the anticoagulated whole blood must also be determined by automated instrumentation (see above).

2. Procedure: as in D.2 above. The result in each well is reported in microgram/L of hemolysate, and then converted into actograms/red cell (where an actogram = $10^{-18}$ grams), by determining the number of red cells in the lysed specimen (hemoglobin$_{lysate}$ × 1/MCH) and dividing the ferritin result by this value.

3. Determination of Underhemoglobinized Red Cells

1. Reagents and instruments: Any instrument incorporating a cytometer capable of measuring cell size and hemoglobin concentration can be used for this assay (for example, the Technicon H-2, Technicon Instruments Corp., Tarrytown, N.Y.). This instrument analyzes red cells by laser beam scattered at two different angles simultaneously to measure both red cell size and hemoglobin concentration. The instrument can report this information either as separate histograms (one for red cell size, another for hemoglobin concentration); or one plot, where red cell size is reported on one axis, and hemoglobin concentration for the same cells on another axis.

2. Procedure: Anticoagulated blood is run through the instrument per manufacturer's instructions, and printouts of both individual, and the combined, histograms are obtained. Hypochromic cells are identified as cells with <28 g/dL hemoglobin.

4. Determination of ZPP: A drop of blood placed on a slide is inserted into a fluorometer dedicated to measuring the ZPP level by comparing the intensity of light generated by ZPP fluorescing at 594 nm, versus the amount of light absorbed by hemoglobin at 420 nM. [Reference: Schifman R. B.) Red blood cell zinc protoporphyrin to evaluate anemia risk in deferred blood donors, *Am. J. Clin. Path.* 87:511–514 (1987)].

1. Reagents and equipment:
   a. Hematofluorometer (AVIV Biomedical Inc., Lakewood, N.J.)
   b. Whole blood, anticoagulated
2. Procedure: Use per manufacturer's instructions. The result assumes a hematocrit of 42%; and direct, linear corrections can be made for higher or lower hematocrit values.

5. Separation of Red Cell Fractions for Determination of Underhemoglobinized Red Cells and ZPP
   1. An anticoagulated whole blood sample is used. This sample is washed twice with a solution containing 130 mM KCl, 10 mN NaCl, 1 mM $MgCl_2$, 1 mM K-phosphate buffer (pH 7.4), and 10 mM glucose. Following the last wash, sufficient solution is added to adjust the hematocrit to 80%.
   2. The washed cells are centrifuged for 1 hour at 37° C. at 15,000 RPM in a Sorvall RC-5B centrifuge using an SS-34 fixed-angle rotor.
   3. The height of the column of cells is measured. The top 15% of cells in the column are aspirated off with a pipette; this fraction is the "top" or "light" fraction of cells.
   4. The middle 35% of cells is discarded The lower 50% is collected; this fraction is the "bottom" or "heavy" fraction.

VI. Experiments and Empirical Data

The experiments and data provided hereinafter are directed to the in-vivo consequences and effects of recombinant human erythropoietin usage and its effects on red blood cell regeneration in non-anemic autologous blood donors. Autologous red cell transfusion is a very attractive alternative to the use of homologous blood in elective surgery. However, the collection of autologous blood units in a quantity sufficient to forestall homologous transfusions is frequently not possible without engendering anemia in the patient-donor. The physiologic limits to red cell regeneration and increased production following repeated phlebotomies are linked to the level of body iron stores; and recent studies of autologous donors have shown that, despite the development of moderate anemia, serum endogenous erythropoietin values and levels rise only minimally. Accordingly, the described experiments and empirical data evaluate the administration of rEPO concomitant with repeated blood donations by each subject under test.

It will be noted and appreciate, however, that the provided empirical data is evidence of the effects of repeated rEPO administration over time; and reveal a methodology which is able to detect, identify, and determine the consequences of using rEPO via a battery of different cell and chemical blood assays—which collectively and cumulatively reveal the use of EPO in a discriminating fashion. Thus, although the experimental study is specified in its scope and intent, the resulting empirical data and evaluations are probative evidence and direct proof of the utility, reliability, and accuracy of the present methodology for the purpose of detecting any use of an exogenous erythropoiesis stimulating agent by a living subject.

This study tested whether the effect of rEPO on autologous donors could be increased with a daily subcutaneous administration schedule. In the process, the characteristics of red blood cells produced under stimulation by rEPO were recognized and the effects of iron stores on the erythroid response were identified.

Study Design and Patient Selection

Simultaneous rEPO and blood donations. Six adult male volunteers (subjects 1–6) in good health, with normal blood counts and total iron stores, participated in a two-armed study (rEPO and control). In the rEPO arm, each subject self-administered rEPO (200 units/kg, kindly supplied by Ortho Pharmaceutical Corporation, Raritan, N.J.) by subcutaneous injection daily for the first 21 days. During this three-week period, each subject also attempted to donate a unit of blood (450 ml±10%) twice a week; blood donation was deferred if the hematocrit fell below 34%. Additional blood was taken for periodic laboratory tests. Blood counts were followed throughout the donation period, and for an additional four weeks. Oral iron supplements (ferrous sulfate, 325 mg TID) were taken by subjects throughout the study period. In the control study, the same protocol was followed except that subcutaneous rEPO was not administered. A minimum six month interval was scheduled between the two arms of this study.

rEPO in advance of blood donations. As in the first study, rEPO (200 units/kg) was administered daily by subcutaneous injection for the first 21 days, and all subjects attempted to make blood donations twice a week over three weeks. However, the three week blood donation period was delayed one week, beginning on Day 8 of the study, and there was no control arm. Four subjects enrolled in this study: Three were adult male volunteers in good health, with normal blood counts and iron stores (Subjects 7–9). The fourth subject (Subject 10) was a 44 year old male with untreated idiopathic hemochromatosis; his condition was diagnosed by iron studies (serum ferritin 5,080 ng/ml) and a liver biopsy demonstrating prominent iron deposition (measured iron 49,952 microgram/g dry weight; normal range 530–900 microgram/g dry weight). This patient also had controlled hypertension, and had suffered a transient ischemic attack 9 months before participation in the study.

Laboratory Measurements

Complete blood counts were measured and determined using the H1-Hemalog (Technicon Instruments, Co., Tarrytown, N.Y.) on blood samples anticoagulated with potassium EDTA. This instrument is preferred because it determines red cell volume and hemoglobin concentration on a cell-by-cell basis using flow cytometry. Arbitrarily established gates (hemoglobin concentration $<28$ and $>41$ g/dl; cell volume $<60$ and $>120$ fl) were used to define the presence of hypochromic and hyperchromic cells, and of micro- and macrocytic cells, respectively. Reticulocytes were identified using new methylene blue stained slides and reported as the absolute number per microliter. Daily red blood cell phlebotomy losses for each subject were measured. These losses consisted of the volume of whole blood collected at each donation, plus blood collected for laboratory testing, multiplied by that day's hematocrit. Each subject's red cell mass was determined based on body weight; an estimated blood volume of 70 ml/kg; and the hematocrit. Red cell production (in excess of baseline) over the first four weeks of the study was then calculated using the following formula:

RBC production = RBC phlebotomy losses$_{(Days\ 1-28)}$ +

(RBC mass$_{Day\ 29}$ − RBC mass$_{Day\ 1}$)

Plasma iron and iron binding capacity were measured by standard techniques conventionally known. Ferritin levels were determined by a fluoroimmunometric assay, and serum erythropoietin levels by radioimmunoasay (Diagnostic Systems Laboratory, Webster, Tex.).

Separation of red cells by density was carried out using the method of Murphy [*J. Lab. Clin. Med.* 82:334–341 (1973)]. In brief, anticoagulated whole blood samples were washed twice with a solution containing 130 mM KCl, 10 mM NaCl, 1 mM MgCl$_2$, 1 mM K-phosphate buffer (pH 7.4), and 10 mM glucose. An 80% cell suspension was prepared, and centrifuged for 1 hour at 37° C. at 15,000 RPM in a Sorvall RC-5B centrifuge using an SS-34 fixed-angle rotor. The height of the column of packed cells was measured, and the 15% top fraction was collected by gentle pipetting. The middle 35% was discarded, and the lower 50% was collected. Zinc protoporphyrin, a measure of iron status in red cells, was determined by fluorometry; the results were expressed as microgram/ml of blood, corrected for a hematocrit of 42% [Lomola et al., *Clin. Chem.* 21:93–97 (1975)].

Statistical Analysis

Group data are expressed as means ±SDs. Two-tailed Student's t tests were used to determine significance ($p < 0.05$).

Results

Of the six subjects enrolled in the two-arm study, four subjects (1–4) participated in the rEPO arm first; the other two subjects (5 and 6) participated in the control arm first. All subjects were of normal weight. Subcutaneous injections of rEPO (at 10,000 units/ml, between 1.3 and 1.8 ml per injection) were associated with mild burning sensations during administration by the subjects. No other complications related to drug therapy were observed. The results are summarized by Table 5.

During the rEPO arm portion of the study, each subject was able to donate 6 units of blood during the three week donation interval (Table E1); during the absence of rEPO administration in the control phase, anemia precluded one or more donations in 5 of the 6 subjects (mean donations 5.0±1). During the rEPO administration stage, the peak reticulocyte count (568±159×10$^9$/l) occurred between Days 11 and 14, and was 2.4 times greater than the individual's peak reticulocyte count without rEPO (235±77×10$^9$/1), which occurred later (between Day 15 and 21). However, the magnitude of reticulocytosis in the rEPO vs. control arm was different for each individual (range 1.2 to 4.7 times greater). Mean reticulocyte counts at the end of each week of the study as shown by FIG. 1A were significantly greater with rEPO administration (during Weeks 1–3) than in the absence of rEPO.

Figure 2A:
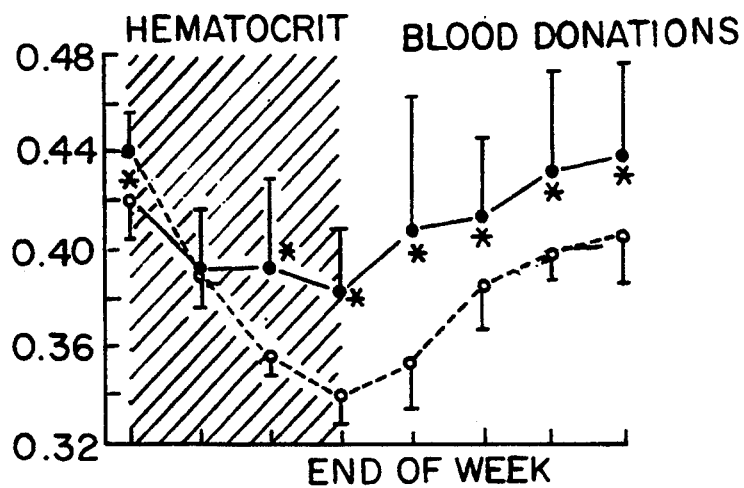
FIGS. 2A-2C are graphs illustrating the hematocrit values at baseline and at the end of each week of the study for each test subject.

Phlebotomy-induced decreases in hematocrit values occurred in these subjects in both arms as illustrated by FIG. 2; the lowest mean hematocrit value occurred during the third week in both parts of the study, but was significantly worse in the control arm (0.34±0.01) than in the rEPO administered arm (0.38±0.03, $p < 0.05$). At the end of the control arm study (end of Week 7), the mean hematocrit (0.41±0.02) had still not returned to original baseline values (0.44±0.02, $p < 0.05$). By contrast, the hematocrit at the end of Week 7 of the rEPO arm (0.44±0.04) was slightly higher than at the start (0.42±0.01, $p < 0.05$) as appears in FIG. 2A.

Figure 1B:
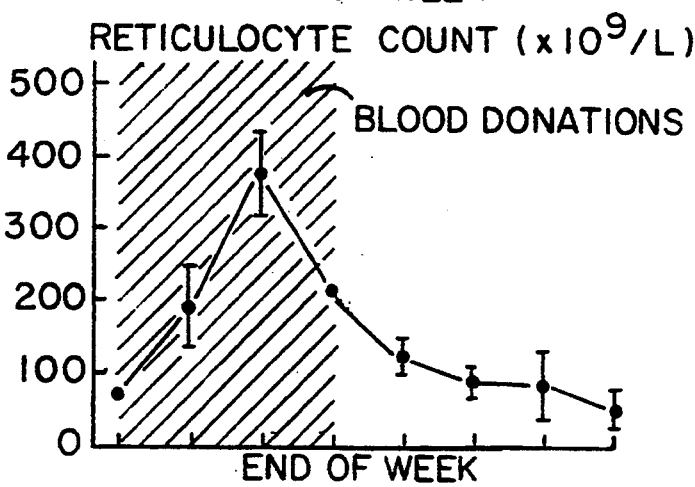
Figure 2B:
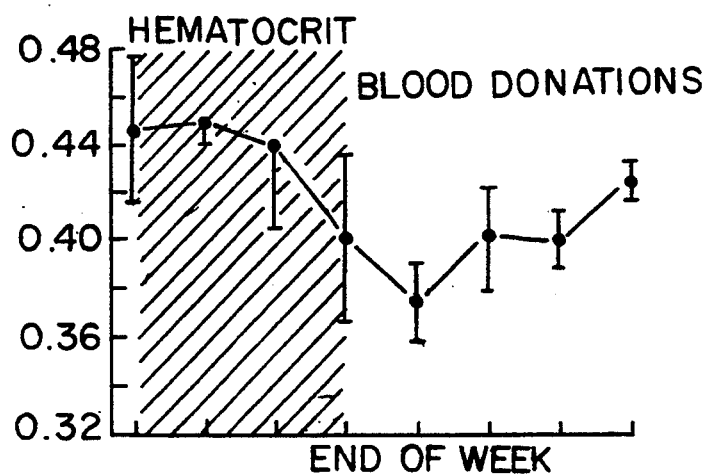

Subjects 7–9 who began rEPO administrations one week in advance of blood donations were also able to donate all 6 units of blood. The mean peak reticulocyte count (493±51×10$^9$/l) occurred in all three subjects following rEPO use on study Day 13, and was lower than the value for subjects 1–6 ($p < 0.05$) as shown by FIG. 1B. Moreover, the reticulocyte count was elevated throughout the period of rEPO administration. However, the hematocrit dropped substantially, and the minimum hematocrit (0.38±0.02) occurred at the end of Week 4, concomitant with the conclusion of blood donations as illustrated by FIG. 2B.

Figure 1C:
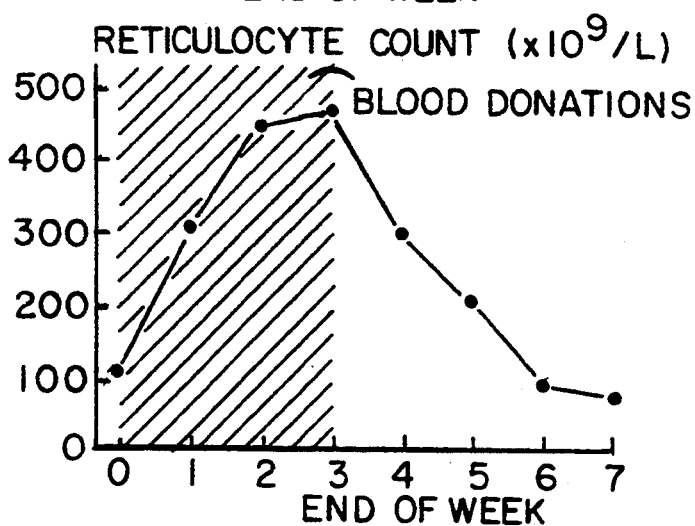
Figure 2C:
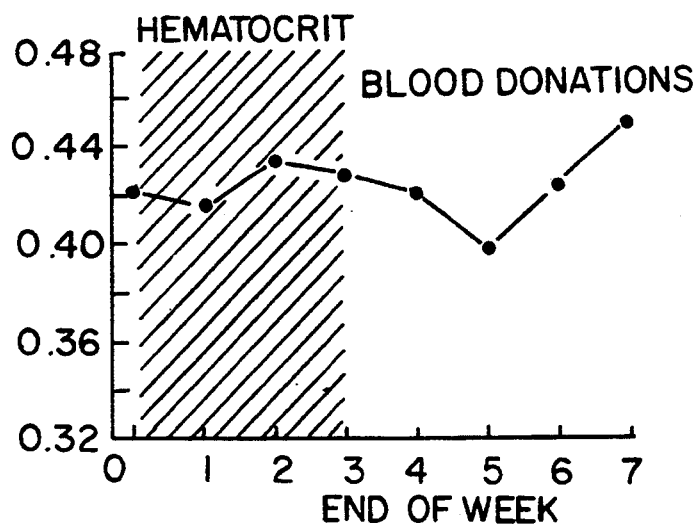

The reticulocyte and hematocrit values for the subject with idiopathic hemochromatosis (Subject 10), are shown by FIGS. 1C and 2C respectively. By protocol, a unit of blood was collected from this patient twice a week during Weeks 2 through 4. However, because of this patient's history of hypertension and transient ischemic attack, additional units of blood were collected (one each during Weeks 2, 4, 5, and 7) in order to keep his hematocrit <46%. As a result, Subject 10 donated 8 units of blood during the 21 day donation period, and 10 units during the entire 7 week study. His peak reticulo-

TABLE 5

Response to rEPO in subjects 1–10. Subject 1–6 participated in a two-arm study, taking subcutaneous rEPO daily for 3 weeks in one arm, and no drug in the control arm. Subjects 7–10 took rEPO for 3 weeks beginning one week ahead of the 3-week donation period. Subject 10 had idiopathic hemochromatosis.
*:p <0.05 (rEPO vs. control result).

| | | | Baseline iron stores | | | | Units donated over 21 days | | Peak reticulocyte count (× 10$^9$/L) | | Red cell production over 28 days (mL) | |
| | | | Iron saturation (%) | | Ferritin (ng/mL) | | | | | | | |
| Subject | Age | Weight (kg) | rEPO | control | rEPO | control | rEPO | control | rEPO | control | rEPO | control |
|---|---|---|---|---|---|---|---|---|---|---|---|---|
| 1 | 35 | 80 | 14% | 46% | 86 | 71 | 6 | 5 | 559 | 119 | 1,234 | 958 |
| 2 | 40 | 80 | 24% | 28% | 103 | 73 | 6 | 6 | 510 | 161 | 1,456 | 840 |
| 3 | 54 | 66 | 27% | 23% | 38 | 76 | 6 | 5 | 908 | 291 | 1,439 | 605 |
| 4 | 53 | 64 | 24% | 39% | 50 | 39 | 6§ | 5 | 545 | 257 | 1,264 | 705 |
| 5 | 29 | 86 | 21% | 58% | 53 | 80 | 6 | 5 | 425 | 351 | 800 | 750 |
| 6 | 36 | 67 | 22% | 22% | 110 | 52 | 6 | 4 | 459 | 233 | 1,052 | 456 |
| Mean | 41±9 | 74±8 | 22±4%* | 36±13% | 73±28 | 65±15 | 6 | 5±1 | 568±159* | 235±77 | 1,208±227* | 719±161 |
| 7 | 28 | 75 | 26% | | 36 | | 6 | | 426 | 766 | | |
| 8 | 42 | 88 | 34% | | 24 | | 6 | | 551 | 1,105 | | |
| 9 | 29 | 73 | 30% | | 38 | | 6 | | 501 | 953 | | |
| Mean | 33±6.4 | 79±6 | 30±3% | | 33±6 | | 6 | | 493±51 | 941±139 | | |
| 10 | 44 | 90 | 80% | | 5,080 | | 8§ | | 868 | 1,764 | | |

§ Additional blood was drawn after the 21 day collection interval because of high hematocrits, from subject 4 (one unit during week 7) and subject 10 (two units, during weeks 5 and 7).

cyte count (868×10⁹/1) also occurred on Day 12. Despite the frequent phlebotomies, his hematocrit never fell below 40%.

Red Cell Production

Red cell production at the end of four weeks, expressed as volume of packed red blood cells, is shown for each subject in Table 5. The volume of red cells generated by Subjects 1–6 while using rEPO (1,208±227 ml) was 68% higher than in the same subjects without use of rEPO (719±161, $p<0.05$). However, results in individual subjects varied. For example, Subject 3 made 2.4 times more red cells with rEPO (1,439 ml) than without (605 ml); while Subject 5 had very little increase in red cells with rEPO (800 ml, versus 750 without rEPO).

In contrast, although Subjects 7, 8, and 9 were able to complete 6 blood donations during the 21 day interval, red cell production was lower (941±139 ml) than for Subjects 1–6 ($p<0.05$). Red cell production was highest (1,764 ml) in the subject with hemochromatosis.

Serum EPO Levels

Serum EPO levels were chemically determined twice a week during the study. During the rEPO administration period, all subjects maintained elevated serum EPO levels (range 190–803 mu/ml). In the six subjects who also participated in the control arm, maximum serum EPO levels occurred at the end of the third week of the study (range 28–60 mu/ml).

Vitamin B$_{12}$ and Folic Acid

Vitamin B$_{12}$ and folic acid levels were measured at the start of the study and at Day 28 (following blood donations). Each subject maintained constant levels of each vitamin throughout the entirety of this period. B$_{12}$ levels were normal in all subjects; and seven of ten subjects had normal folate levels. Three subjects had borderline or low folate levels (normal value $\geq 2.0$ ng/ml): Subject 1 with rEPO: 1.2 ng/ml (Day 1), 1.1 ng/ml (Day 28); without rEPO: 1.4 ng/ml (Day 1), 2.4 ng/ml (Day 28); Subject 5 with rEPO: 2.2 ng/ml (Day 1), 1.9 ng/ml (Day 28); without rEPO: 2.1 ng/ml (Day 1), 2.4 ng/ml (Day 28); and Subject 9 with rEPO: 1.4 ng/ml (Day 1), 1.6 ng/ml (Day 28).

Iron Stores

Figure 3A:
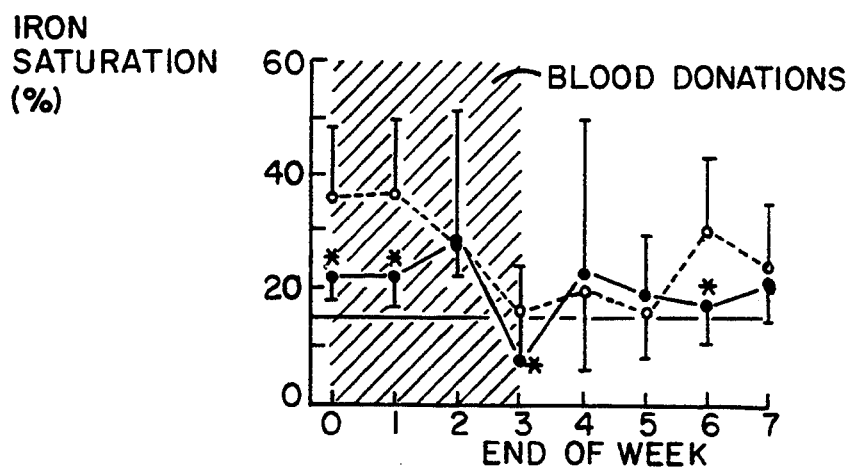
FIGS. 3A-3C are graphs illustrating the iron saturation values at baseline and at the end of each week of the study for each test subject.
Figure 3B:
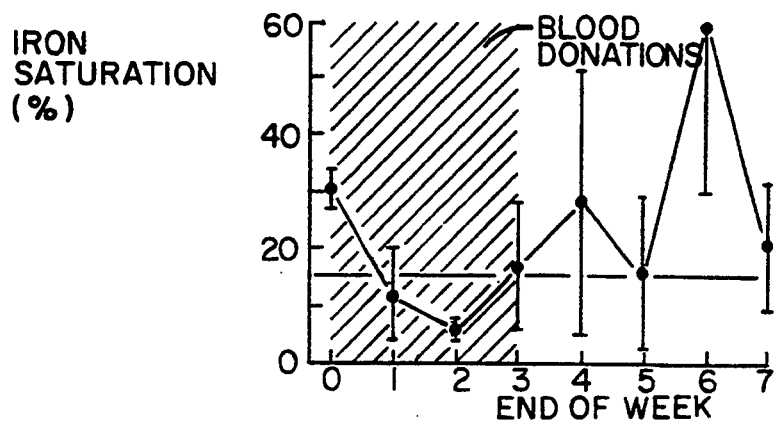
Figure 3C:
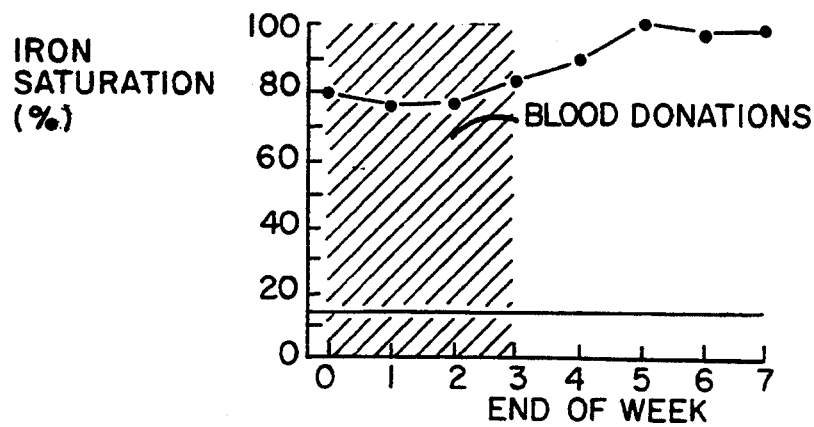
Figure 4A:
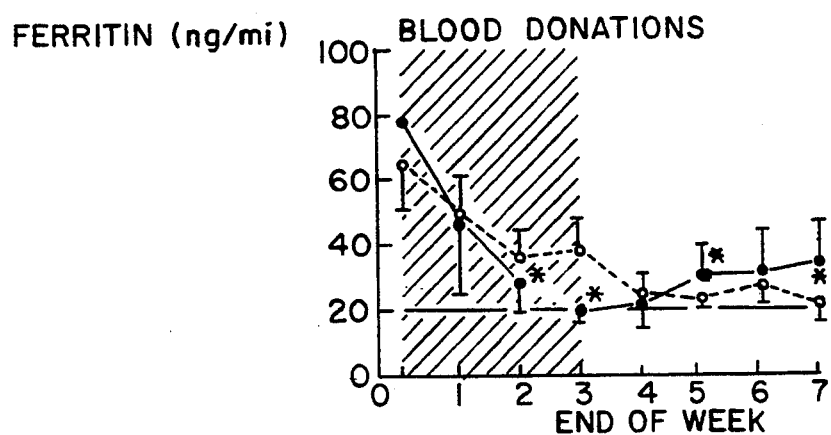
FIGS. 4A-4C are graphs illustrating the ferritin values at baseline and at the end of each week of the study for each test subject.
Figure 4B:
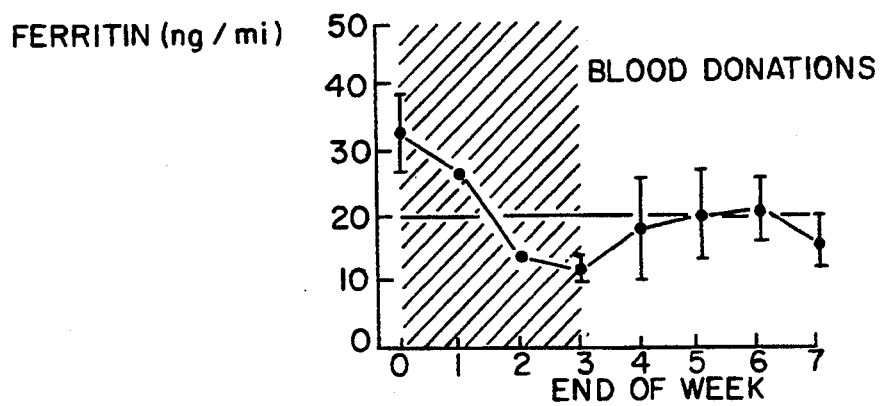
Figure 4C:
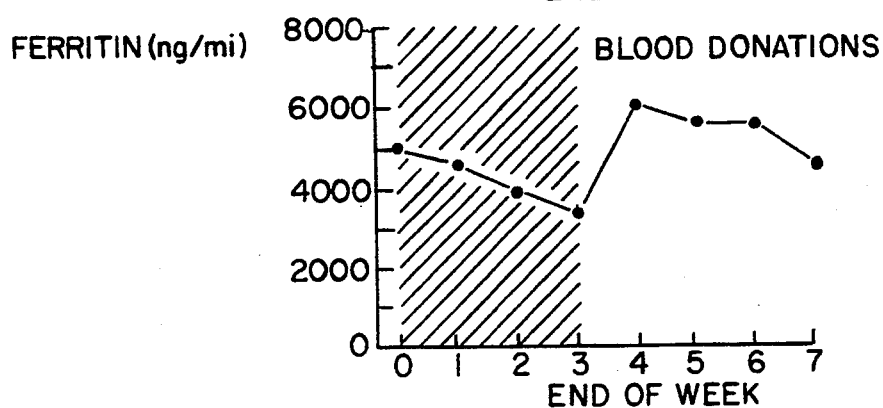
Figure 5:
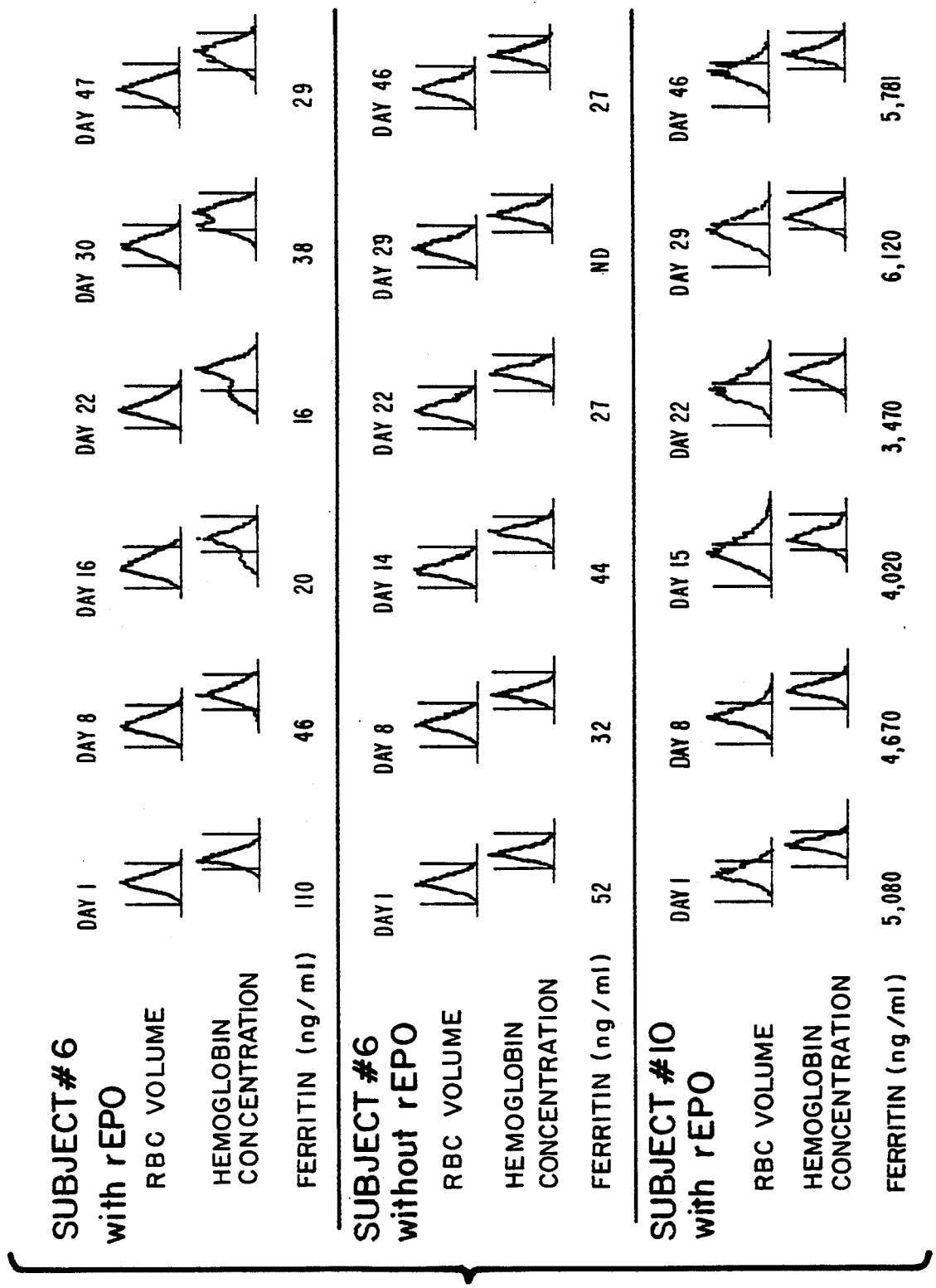
FIG. 5 illustrates the red blood cell volume histograms, the hemoglobin concentration histograms, and the ferritin determinations for subjects 6 and 10 over time.

Percent saturation of transferrin (iron saturation) and serum ferritin levels for the study groups are shown in Table E1 (baseline values) and by FIGS. 3 and 4 (values over time). Baselin iron stores were normal at the beginning of each study arm (iron saturation $>15\%$; ferritin $>20$ ng/ml) in Subjects 2–9. Subject 1 had a borderline iron saturation value (14%) but a normal ferritin level (86 ng/ml) at the start of the rEPO arm phase and normal values during the control study. Abnormal values for iron saturation and ferritin occurred in Subjects 1–6 during rEPO administration by the end of the third week as shown in FIGS. 3A and 4A. Without administration of rEPO, mean iron saturation and ferritin levels fell, but were never below normal range values. In Subjects 7–9, mean iron saturation was abnormal by the end of the first week, and mean ferritin levels by the end of Week 2 were as shown by FIGS. 3B and 4B. Iron saturation in the patient with hemochromatosis (Subject 10) was markedly elevated at the start of the study (80%) and rose to 100% following discontinuation of rEPO administration (FIGS. 3C and 4C). His baseline ferritin level (5,080 ng/ml) fell by 30% (to 3,470 ng/ml) during rEPO administration; and then rebounded (6,120 ng/ml at the end of Week 4; 4,681 ng/ml at the end of Week 7).

Red Cell Size and Hemoglobin Distribution

Figure 6:
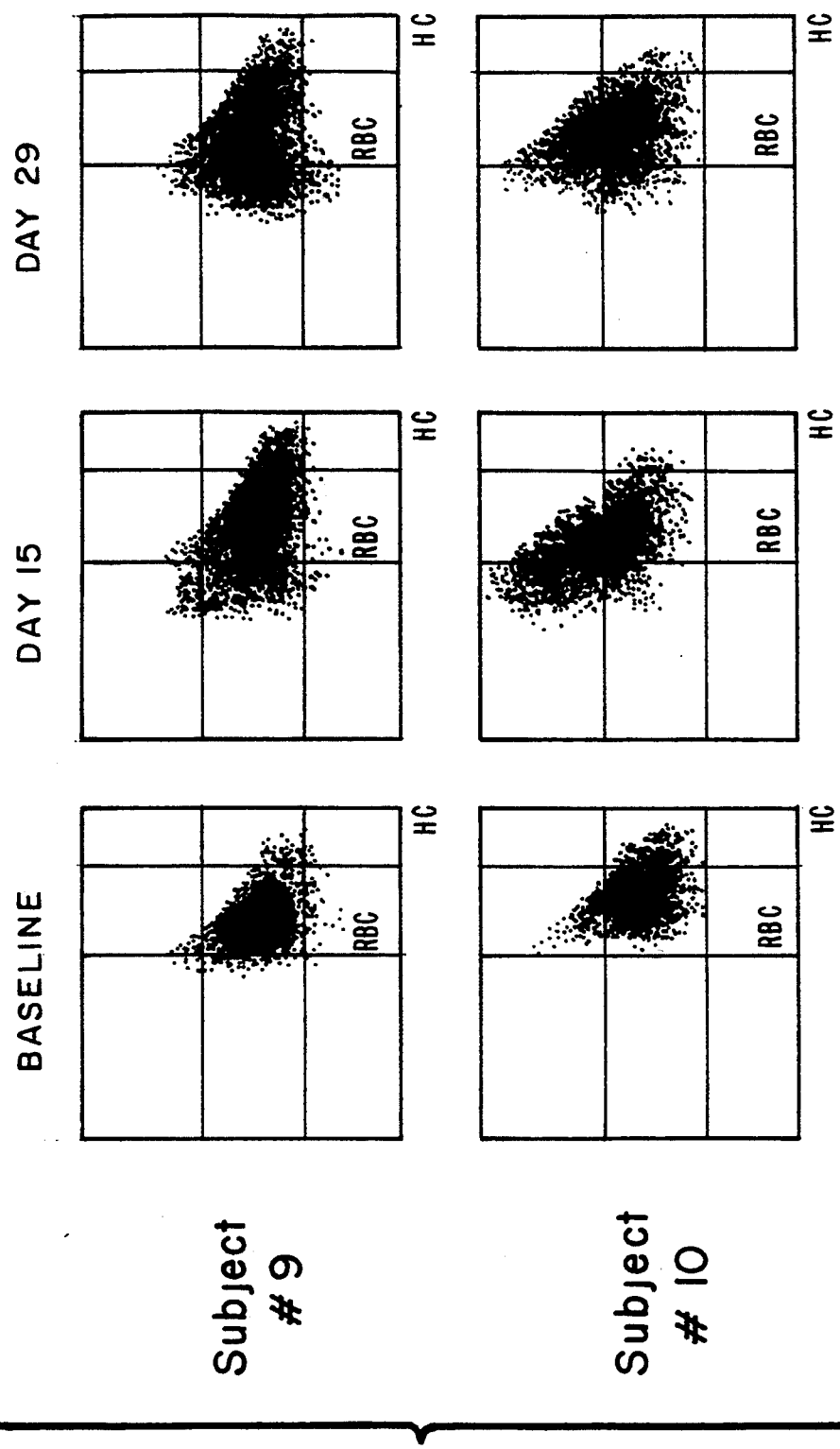
FIG. 6 illustrates two-dimensional histograms of hemoglobin concentration (HC, X-axis) vs red cell volume (V, Y-axis) in subjects 9 and 10 over time.

Red cell size and hemoglobin concentration histograms generated by the Technicon H-1 blood analyzer were obtained daily in 8 of the 10 subjects (note that histograms are not available for Subjects 1 and 4). In normal subjects taking rEPO, but not in the subject with hemochromatosis, an elongated shoulder profile due to markedly hypochromic cells with hemoglobin concentrations as low as 20 g/dl was identified on the hemoglobin concentrationhistogram by Day 7 or 8. Representative red cell size and hemoglobin histograms from Subject 6 with normal iron stores both with and without rEPO are shown by FIGS. 6A and 6B. Histograms for Subject 10 (with hemochromatosis) are shown in FIG. 6C.

As shown by Subject 6, the hypochromic shoulder in the hemoglobin histogram developed at a time when the ferritin (46 ng/ml) (and iron saturation (22%) were still normal values. In all subjects, the hypochromic shoulder became a distinct second peak over the second week of the study; and maximum cell size was attained by the end of the fourth week. The two peaks merged by the end of the sixth week. The red cell volume histogram retained a unimodal shape, although a tail of macrocytic cells emerged during the rEPO administration period. Note, however, that the hypochromic cell peak was not detected in subjects who donated blood without using rEPO. Subject 10 (with iron overload) developed a prominent macrocytic tail on the red cell volume histogram and a smaller hypochromic tail on the hemoglobin concentration histogram, but a unimodal distribution was maintained. This is seen in FIG. 6C.

Figures 1, 7A:
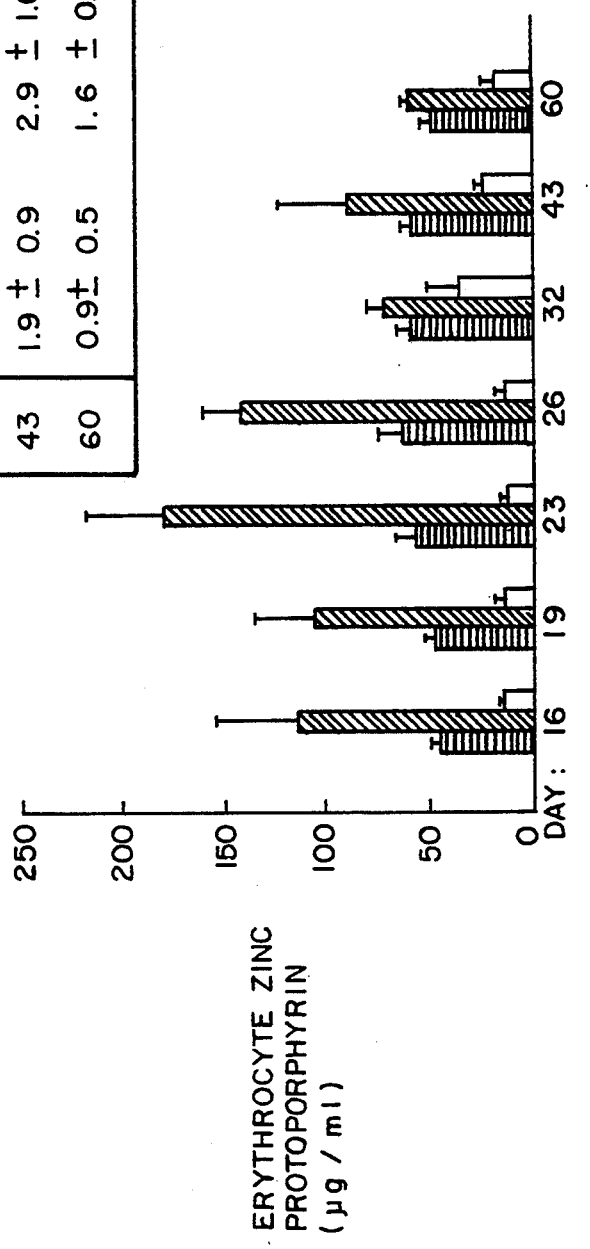
FIGS. 7A and 7B illustrate the zinc protoporphyrin values in whole blood and density separated fractions for subjects 7-10.
Figures 1, 7B:
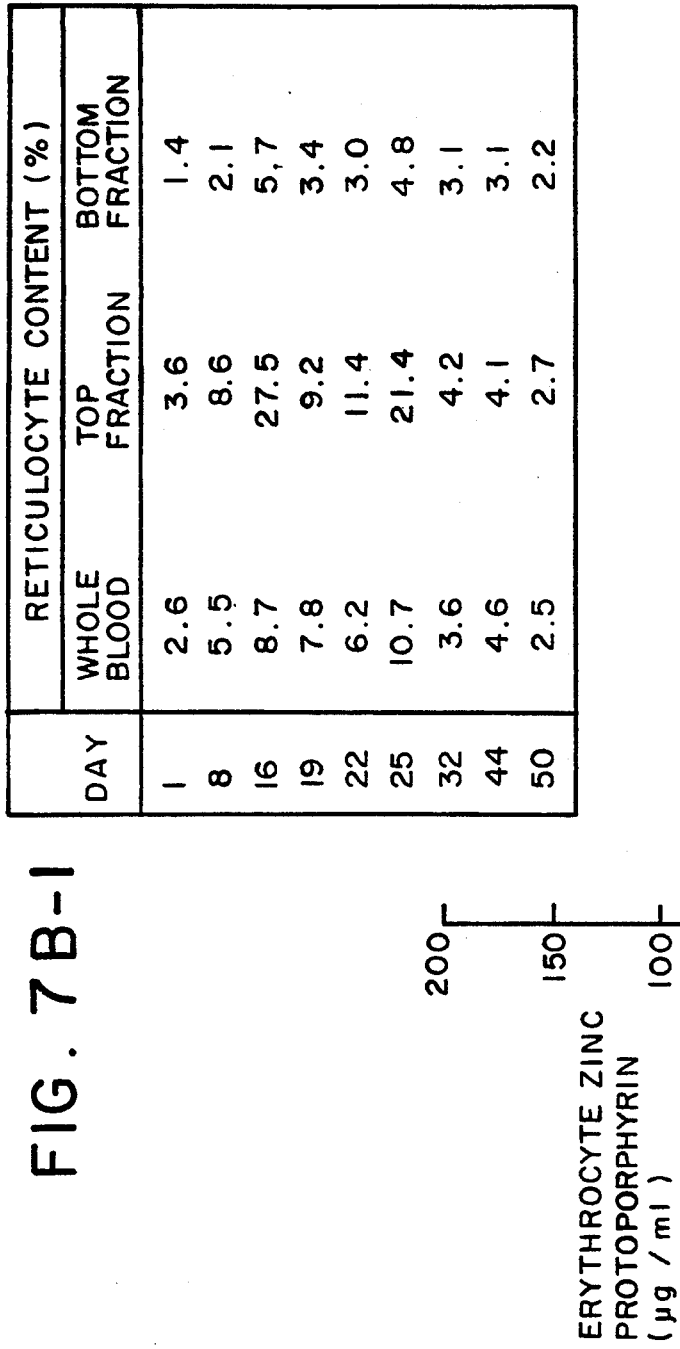

Correlation of the volume and hemoglobin concentration of individual red cells on a two-dimensional plot is shown in FIG. 7 for a representative subject with normal baseline iron stores (Subject 9) and the subject with idiopathic hemochromatosis (Subject 10). The normal distribution of red cells on this plot resembles a teardrop as appears in the baseline pattern. Reticulocytes are present in the tail, in the top left side of the middle quadrant of each plot. Older cells, which become progressively normocytic and normochromic due to dehydration and loss of potassium and membrane surface in excess of hemoglobin, are more centrally located in this quadrant [Fossat et al., Arch. Pathol. Lab. Med. 111:1150–1154 (1987)]. This pattern is seen in both subjects at baseline.

However, in Subject 9, on Day 15, the new cell population appeared as a bulge on the left side of the teardrop (left middle quadrant); the majority of these cells were hypochromic (hemoglobin concentration $<28$ gr/dl) but not macrocytic (volume $<120$ dl). By Day 29, the proportion of hypochromic cells was greater, and the bulge had shifted downward as cells became more microcytic. Remnants of the hypochromic population were identifiable on these plots throughout the remainder of the seven week study. By contrast, Subject 10 developed a large increase in cells in the upper left and middle quadrants (macrocytic, hypochromic cells) consistent with reticulocytes by Day 15; however, the normal teardrop outline of the histogram was preserved here and on Day 29.

Density Separation of Hypochromic Red Cells

To determine whether the underhemoglobinized red cells produced during rEPO treatment were due to iron-deficient erythropoiesis, fractionation of whole blood samples by density separation was carried out in Subjects 7–9 and the Subject 10 with hemochromatosis.

The lightest 15% of cells (the top fraction, containing almost exclusively hypochromic red cells) was compared to the densest 50% of red cells (the bottom fraction) and to unseparated whole blood for the proportion of reticulocytes and zinc protoporphyrin (ZPP) levels. The results are seen in FIG. 8. Top fraction cells were enriched in reticulocytes in all subjects; the highest concentrations of reticulocytes were found during the first four weeks of the study. In the three normal subjects, ZPP levels in unfractionated whole blood and bottom fraction (dense) cells were normal (<79 micrograms/dl) at all time points. ZPP levels in the light fraction were >100 micrograms/dl on Days 16, 19, 23, and 26, but were lower on subsequent assays (Days 32, 43, and 60). No elevations in ZPP levels were seen at any time point in whole blood or density-separated fractions in the patient with idiopathic hemochromatosis.

Conclusions

1. The effect of daily subcutaneous rEPO (1,400 units/kg/week) on erythropoiesis and reticulocyte increases was substantial, with very high peak reticulocyte counts occuring throughout the entire rEPO administration period. Although phlebotomy-induced anemia marginally can increase the erythropoietic rate, the additional effect of rEPO was demonstrated in Subjects 1-6, who served as their own controls. In this group, the mean peak reticulocyte count during the rEPO study was 2.4 times greater than during the control arm (blood donations with rEPO). Mean red cell production was also significantly better with rEPO (1,207±277 ml, vs 719 ml±161).

2. Despite increased red cell production resulting subcutaneous rEPO administration, the hematocrits of Subjects 1-6 fell markedly. However, because a lag of 4 or more days is seen between the initiation of rEPO use and appearance of increased numbers of reticulocytes in humans, it was possible that an administration schedule in which rEPO was given before actual blood donation might reduce or eliminate the anemia. However, even when rEPO was started seven days in advance of the blood donation period, red cell anemia did not improve, and a marked decrease of hematocrit values occurred by the end of the donation period (end of Week 4).

3. B and folate levels did not change in individual subjects during the blood donation period. However, despite the proven presence of normal iron stores in all subjects at the start of each study, as well as the use of supplemental ferrous sulfate during the blood donation protocol, all subjects showed a loss of iron stores, and that rEPO markedly hastened this depletion. Mean values for iron saturation and ferritin in Subjects 1-6 were abnormal by the third week of the rEPO arm study. In Subjects 7-9, even though blood donations were delayed for one week following institution of rEPO use, the mean iron saturation value became abnormally low by the end of the first week and the mean ferritin value was abnormal by the end of the second week. Iron stores in this group of Subjects 7-9 had a lower mean baseline ferritin (33±6 ng/ml) than Subjects 1-6 (78±23 ng/ml, $p<0.05$). Quantitatively lower iron stores also explain the lower red cell production by Day 28 in Subjects 7-9 as compared to Subjects 1-6. Only Subject 10 with iron overload had no drop in iron saturation levels throughout the study, although his ferritin level fell 30% during rEPO administration.

4. It is noteworthy to recognize that the development of iron deficiency occurs in stages: first, body iron stories are depleted, reflected by a fall in serum ferritin; then transferrin saturation becomes abnormal; and finally anemia develops. Red cells with a low MCHC are usually not seen until this final stage. Although our normal subjects taking rEPO eventually became iron-deficient from the many blood donations, it was most surprising to identify markedly underhemoglobinized red cells promptly following rEPO administration (1-2 days); and to observe these underhemoglobinized cells often in advance of other laboratory evidence of iron deficiency. Moreover, the hypochromic cells which appeared concurrent with rEPO treatment were normocytic and therefore undersized for normal reticulocytes; and they formed distinct separate peaks on the red cell histograms revealing an abrupt decrement in hemoglobin synthesis. In further support of this conclusion, all the hypochromic cells in rEPO-treated normal Subjects 7-9 were iron-deficient, as demonstrated by elevated ZPP levels in the light fraction cells, but not in their whole blood. Protoporphyrins chelated to zinc instead of iron are normally present in the red cell (including reticulocytes) in only very low concentrations; the concentration of ZPP increases in the setting of iron deficiency. In contrast to our normal subjects, only Subject 10 with idiopathic hemochromatosis had normal ZPP levels in his reticulocyte-enriched fractions.

The present invention is not to be restricted in form nor limited in scope except by the claims appended hereto.

What we claim is:

1. An in-vitro method for identifying the surreptitious use of an exogenous erythropoiesis stimulating agent to generate an increase in red blood cell production in a living normal subject, said method comprising the steps of:

obtaining an aliquot of the blood circulating within the living subject;

testing said aliquot of blood to establish an absence of anemia in the living subject, said testing comprising determining at least one parameter selected from the group consisting of hematocrit value and blood hemoglobin concentration, a test result that lies within the normal range of values for said at least one parameter establishing the absence of anemia in the subject;

evaluating said aliquot of blood to establish the presence of at least normal total body iron stores in the living subject, said evaluating comprising the determination of at least one indicator selected from the group consisting of serum iron value, serum transferrin value, serum transferrin saturation, serum ferritin value, and red blood cell ferritin concentration, a determined result that lies within the normal range of values for said at least one indicator establishing the presence of said at least normal total body iron stores in the subject; and analyzing said aliquot of blood to establish the presence of at least one abnormality within the individual red blood cells of the living subject, said at least one abnormality being at least one selected from the group consisting of a less than normal concentration of hemoglobin within individual red blood cells and a greater than normal content of zinc protoporphyrin within individual red blood cells, whereby the established absence of anemia, and the established presence at least normal total body iron stores, and the established presence of said at least one abnormality within individual red blood cells identify that normal living subject as a surreptitious user.

2. The method as recited in claim 1 wherein said exogenous erythropoiesis stimulating agent is one selected from the group consisting of erythropoietin, recombinant erythropoietin, active fragments of erythropoietin, active fused fractions of erythropoietin, active analogs of erythropoietin, and active derivatives of erythropoietin.

3. The method as recited in claim 1 wherein said exogenous erythropoietin stimulating agent is a water soluble salt of a transition metal selected from the group consisting of manganese, cobalt, nickel titanium, vanadium, and chromium.

4. The method as recited in claim 1 wherein said living subject is a human.

5. The method as recited in claim 1 wherein said living subject is an animal.

* * * * *